(12) United States Patent
Firmbach et al.

(10) Patent No.: US 12,324,751 B2
(45) Date of Patent: Jun. 10, 2025

(54) MULTIPURPOSE MEASUREMENT INSTRUMENT FOR USE IN A KNEE-JOINT REPLACEMENT OPERATION

(71) Applicant: Aesculap AG, Tuttlingen (DE)

(72) Inventors: Franz-Peter Firmbach, Emmingen-Liptingen (DE); Svenja Anhorn, Heroldstatt (DE)

(73) Assignee: Aesculap AG, Tuttlingen (DE)

( * ) Notice: Subject to any disclaimer, the term of this patent is extended or adjusted under 35 U.S.C. 154(b) by 321 days.

(21) Appl. No.: 18/124,742

(22) Filed: Mar. 22, 2023

(65) Prior Publication Data

US 2023/0320870 A1 Oct. 12, 2023

(30) Foreign Application Priority Data

Apr. 6, 2022 (DE) .................. 10 2022 203 411.2

(51) Int. Cl.
*A61B 90/00* (2016.01)
*A61F 2/46* (2006.01)
*A61F 2/38* (2006.01)

(52) U.S. Cl.
CPC .......... *A61F 2/4657* (2013.01); *A61F 2/3859* (2013.01); *A61F 2/389* (2013.01); *A61F 2002/4658* (2013.01); *A61F 2002/4661* (2013.01)

(58) Field of Classification Search
CPC ............ A61F 2/4657; A61F 2002/4658; A61F 2002/4661; A61F 2/38; A61F 2/3859; A61F 2/389; A61F 2002/4668; A61B 2090/061; A61B 5/1072; A61B 90/06; A61B 2017/0023; A61B 2017/00473; A61B 2505/05; A61B 5/4504; A61B 5/4528; A61B 5/4585
See application file for complete search history.

(56) References Cited

U.S. PATENT DOCUMENTS

| 10,582,982 | B2 | 3/2020 | Fisher et al. |
| 2016/0030053 | A1 | 2/2016 | Yager et al. |
| 2016/0278873 | A1* | 9/2016 | Fisher .................... A61B 90/06 |

FOREIGN PATENT DOCUMENTS

CN 211094130 U 7/2020

* cited by examiner

*Primary Examiner* — Samuel S Hanna
(74) *Attorney, Agent, or Firm* — Christopher A. Rothe; CM Law

(57) ABSTRACT

A measurement instrument for use in knee-joint replacement includes a rod and a first jaw. The first jaw has a first inner surface that bears on a front face of a bone resection. A slide is guided on the rod and has a second jaw. The second jaw has a second inner surface oriented counter to the first inner surface. The second inner surface bears on a rear face of the bone resection. A scale between the rod and slide indicates a thickness of the bone resection. A continuation part is connected to the first jaw and has a third inner surface that bears on a proximal tibia. The second jaw has a second outer surface oriented counter to the second inner surface. The second outer surface bears on a distal femur. The scale indicates a longitudinal distance between the distal femur and the proximal tibia.

7 Claims, 3 Drawing Sheets

MULTIPURPOSE MEASUREMENT INSTRUMENT FOR USE IN A KNEE-JOINT REPLACEMENT OPERATION

CROSS-REFERENCE TO RELATED APPLICATION(S)

This application claims priority under 35 U.S.C. § 119 to German Application No. 10 2022 203 411.2, filed Apr. 6, 2022, the content of which is incorporated by reference herein in its entirety.

FIELD

The invention relates to a multipurpose measurement instrument for use in a knee-joint replacement operation, having a rod which extends along a longitudinal axis and at one end has a first jaw protruding along a transverse axis, wherein the first jaw has a first inner surface which extends parallel to the transverse axis and which is configured to bear on a front face of a bone resection, a slide which is guided linearly movably on the rod along the longitudinal axis and at one end has a second jaw protruding along the transverse axis, wherein the second jaw has a second inner surface which extends parallel to the transverse axis and which is oriented counter to the first inner surface and is configured to bear on a rear face of the bone resection, and having a scale which is formed between the rod and the slide and is configured at least to indicate a thickness of the bone resection along the longitudinal axis.

BACKGROUND

The use of orthopaedic prostheses as artificial replacements for damaged or worn natural bone structures of a patient is common medical practice. In particular, hip joint and knee joint replacement operations are nowadays routine in surgical orthopaedics.

In a knee-joint replacement operation, or total knee arthroplasty (TKA), joint surfaces of the femur and/or tibia that have become worn or have been otherwise affected by disease or by injury are replaced by a knee joint prosthesis. Such knee joint prostheses usually comprise a femoral component, which is implanted at the distal end of the femur, and a tibial component, which is implanted at the proximal end of the tibia. In order to ensure perfect functioning of the artificial replacement joint, the aforementioned components have to be placed as precisely as possible in a defined position and orientation with respect to the anatomy of the patient and to the axes of the body. Otherwise, a result must be expected that is unsatisfactory for the patient. There are different surgical approaches as regards the positioning of the components.

In an approach known as mechanical alignment, which has been the approach mainly used hitherto, the position and orientation of the artificial joint axes of the knee joint prosthesis have been provided so as to be mechanically ideal, without consideration being given to any orthopaedic deformities presented by the patient. The longitudinal axis of the tibia has often been used here as a reference axis for the orientation and positioning. Clinical studies have shown that the mechanical alignment approach can lead to the function of the artificial knee joint being felt unnatural.

A further approach is what is known as kinematic alignment. In this technique, the femoral component and the tibial component are positioned taking into consideration any orthopaedic deformities presented by the patient. The aim is to restore the patient's natural joint orientation, which in some cases is affected by deformity. Clinical studies have shown that the kinematic alignment approach is often associated with improved patient satisfaction. In particular, the function of the artificial knee joint is felt by the patient to be more natural.

With the aim of further improving patient satisfaction, there is a fundamental need for surgical instruments that are as precise as possible, easy to use and cost effective for the implementation of kinematic alignment.

The present invention deals with such surgical instruments, more precisely with a multipurpose measurement instrument for use in a kinematic alignment TKA.

Such a multipurpose measurement instrument is known from U.S. Pat. No. 10,582,982 B2 and is provided for use in a knee-joint replacement operation using the kinematic alignment approach. The known multipurpose measurement instrument has an elongate rod and a slide which is guided linearly movably along the longitudinal axis of the rod. The rod has at one end a first jaw which protrudes along a transverse axis and which has a first inner surface. The first inner surface is configured to bear on a front face of a femoral bone resection. For this purpose, the slide correspondingly has a second jaw having a second inner surface which is oriented counter to the first inner surface and which is configured to bear on a rear face of the femoral bone resection. Furthermore, the known multipurpose measurement instrument has a first scale. The latter is assigned to the first inner surface and the second inner surface and is configured to indicate a thickness, along the longitudinal axis, of the femoral bone resection located between the jaws. The known multipurpose measurement instrument moreover permits the measurement of what is called the AP offset between the distal femur and the proximal tibia. The AP offset designates the distance between distal femur and proximal tibia along the anterior-posterior axis, the measurement taking place under flexion. For this purpose, the known multipurpose measurement instrument has a third jaw, which is arranged on the rod and which protrudes from one end of the rod along the transverse axis counter to the first jaw. To measure the AP offset, an end face of the third jaw is placed onto the proximal tibia, and a second outer surface of the second jaw, directed away from the second inner surface, is placed onto the distal femur. A second scale is present in order to indicate the AP offset. This second scale is arranged on a rear face of the multipurpose measurement instrument directed away from the first scale. Furthermore, the known multipurpose measurement instrument is designed as a disposable item and hence intended to be used just once.

SUMMARY

The object of the invention is to make available a multipurpose measurement instrument of the type mentioned at the outset, which has a simplified design and can be produced and used in a cost-efficient manner.

This object is achieved by the fact that a continuation part is connected releasably to the first jaw, wherein the continuation part has a third inner surface which is configured to bear on a proximal tibia and which extends parallel to the transverse axis and protrudes further from the rod than does the first inner surface, and the second jaw has a second outer surface which extends parallel to the transverse axis and which is oriented counter to the second inner surface and is configured to bear on a distal femur, wherein on the one hand the third inner surface and the first inner surface and on the other hand the second inner surface and the second outer surface are in each case spaced apart from each other along the longitudinal axis by an identical distance, as a result of which the scale is additionally configured to indicate a longitudinal distance between the distal femur and the proximal tibia. By virtue of the solution according to the invention, it is possible to dispense with a further scale for indicating the longitudinal distance between the proximal tibia and the distal femur, i.e. the AP offset. This is achieved according to the invention by the paired identical spacing between the third and first inner surface on the one hand and between the second inner surface and second outer surface on the other hand. In this way, the scale is configured and/or suitable for indicating both the thickness of the bone resection and the AP offset. Compared to solutions known from the prior art with two separate scales, cost advantages are achieved in the production of the multipurpose measurement instrument. There is also simplified handling of the multipurpose measurement instrument. Since only a single scale is present, reading errors are avoided. Such reading errors are in principle conceivable in solutions known from the prior art, for example by the AP offset being read off using the scale configured for the thickness measurement, or vice versa. An incorrect assignment of this kind is ruled out in the solution according to the invention. Moreover, the continuation part that is present according to the invention permits a particularly flexible and thus cost-efficient use of the multipurpose measurement instrument. The continuation part is for this purpose connected releasably to the first jaw. In this way, the multipurpose measurement instrument according to the invention can be easily changed between a first configuration and a second configuration. In the first configuration, the continuation part is releasably connected to the first jaw. In the second configuration, the continuation part is released from the first jaw. The first configuration serves for measurement of the AP offset. For this purpose, the third inner surface of the continuation part protrudes from the rod along the transverse axis further than the first inner surface. To put it simply, the continuation part functions as a kind of elongation of the first jaw. In this way, the third inner surface can be placed on the proximal tibia in order to measure the AP offset, with the second outer surface at the same time bearing on the distal femur. By contrast, the first inner surface does not protrude far enough for this purpose from the rod. Therefore, a measurement of the AP offset is not possible with corresponding bearing of the first inner surface and of the second outer surface. In the second configuration, the continuation part is released from the first jaw. This configuration of the multipurpose measurement instrument serves for measurement of the thickness of the bone resection. Preferably, the third inner surface protrudes over the second inner surface in such a way that a thickness measurement between said inner surfaces is not possible. In this way, incorrect measurements resulting from improper use of the continuation part for thickness measurement are avoided. The releasable connection to the first jaw ensures simple removal and attachment of the continuation part. In different embodiments, the continuation part is connected releasably to the first jaw in different ways, for example by means of a clamping, latching or plug-in connection.

In one embodiment of the invention, the continuation part is connected to the first jaw by means of a first joining connection that is releasable without tools and connectable without tools. Releasable without tools means that no tool of any kind is needed to release the first joining connection. Accordingly, connectable without tools means that no tool of any kind is needed for connecting the first joining connection. Therefore, the continuation part in this embodiment of the invention can be attached to and/or removed from the first jaw without tools. As a result, the set-up and handling of the multipurpose measurement instrument are further simplified. In particular, time can be saved when changing between said different configurations of the multipurpose measurement instrument.

In one embodiment of the invention, the first joining connection has at least a first bore and a first pin element which are releasably plugged together orthogonally with respect to the longitudinal axis and the transverse axis, wherein the first bore is introduced into the first jaw and the first pin element is rigidly connected to the continuation part, or vice versa. This embodiment is particularly easy to produce and permits a robust and reliable releasable connection of the continuation part to the first jaw. In this embodiment, the first joining connection is a releasable plug-in connection between the first bore and the first pin element. The plug-in connection is formed between an inner circumference of the first bore and an outer circumference of the first pin element. The outer circumference is preferably slightly greater than the inner circumference. This results in a transition fit and/or interference fit, which leads to a reliable and sufficiently strong releasable connection.

In one embodiment of the invention, the second outer surface is formed on an extension part connected releasably to the second jaw, wherein the second jaw has an inclined and/or curved outer contour which is not configured to bear on the distal femur and which is covered at least in part by means of the second outer surface. The measurement of the AP offset, i.e. the longitudinal distance between the distal femur and the proximal tibia, requires the second outer surface and the third inner surface to bear in the correct manner. For this purpose, said surfaces each extend parallel to the transverse axis, i.e. orthogonally with respect to the longitudinal axis. By contrast, a curved or inclined longitudinal extent that deviates from this does not allow them to bear in the correct manner and, consequently, does not permit measurement of the AP offset. The inventors have found that commercially available arrangements composed of rod and slide, as may be used in principle for producing the multipurpose measurement instrument according to the invention, often have a second jaw that is curved or inclined to the outside in relation to the transverse axis. Therefore, the outer contour of the second jaw is not suitable for measuring the AP offset. By means of the extension part, commercially available arrangements of this kind can easily be enabled to measure the AP offset. Since the second outer surface at least partially covers the outer contour of the second jaw, the second outer surface of the extension part, instead of the outer contour of the second jaw, comes to bear on the distal femur in order to permit measurement of the AP offset.

In one embodiment of the invention, the extension part is connected to the second jaw by means of a second joining connection that is releasable without tools and connectable without tools. In this way, the extension part can be attached to and removed from the second jaw in a particularly simple and time-saving manner. To avoid repetition, reference is made to the above disclosure concerning the first joining connection releasable without tools and connectable without tools. The disclosure regarding the first joining connection also applies, mutatis mutandis, to the second joining connection.

In one embodiment of the invention, the second joining connection has at least a second bore and a second pin element which are releasably plugged together orthogonally with respect to the longitudinal axis and the transverse axis, wherein the second bore is introduced into the second jaw, and the second pin element is rigidly connected to the extension part, or vice versa. The advantages ensuing from this design of the second joining connection correspond to those of the corresponding design of the first joining connection. To avoid repetition, reference is made to the relevant disclosure. The disclosure regarding the corresponding design of the first joining connection also applies, mutatis mutandis, to this embodiment of the invention.

In one embodiment of the invention, the rod and the slide are each made of metal and are configured for repeated use, and the continuation part and/or the extension part are/is made of plastic and configured to be used just once, i.e., as disposable part. The fact that the arrangement composed of the rod and of the slide can be used multiple times brings cost advantages and has a reduced impact on the environment. This is in contrast to solutions known from the prior art in which the entire multipurpose measurement instrument is designed as a disposable item to be used just once.

BRIEF DESCRIPTION OF THE DRAWINGS

Further advantages and features of the invention will become clear from the following description of preferred illustrative embodiments of the invention, which are explained with reference to the drawings.

DETAILED DESCRIPTION

Figure 1:
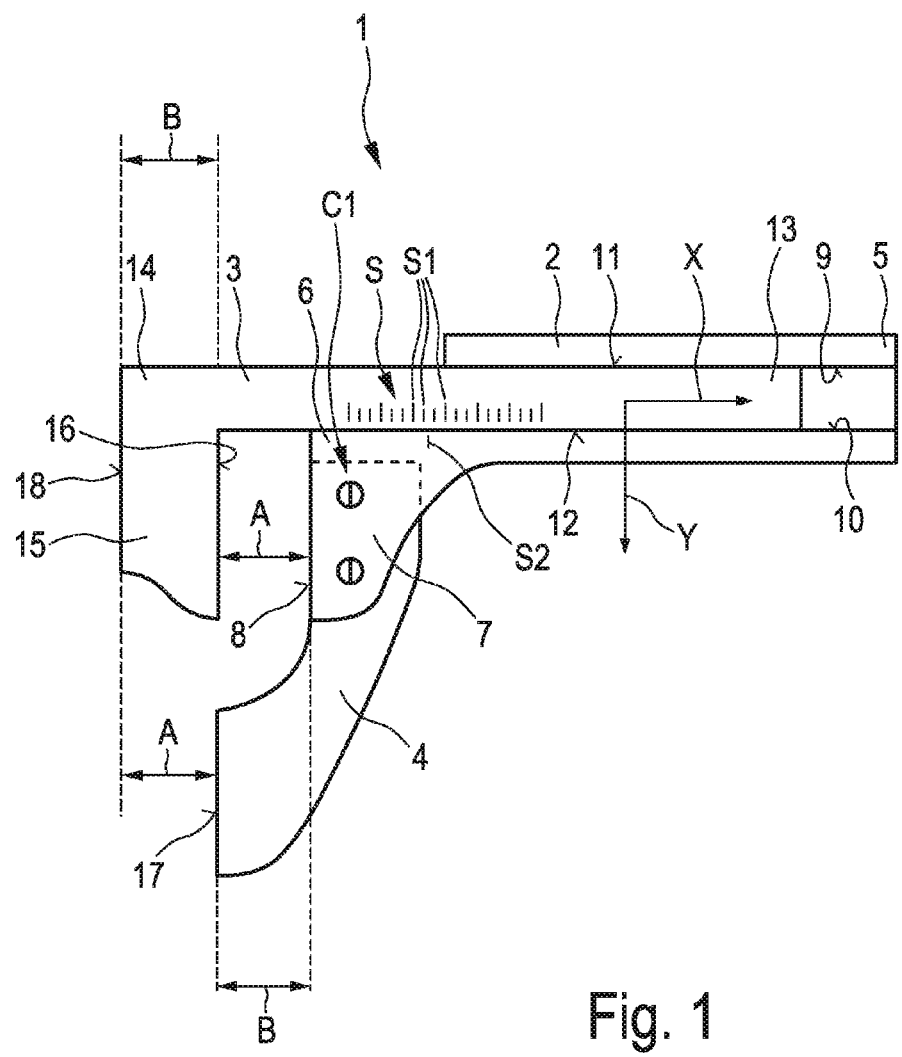
FIG. 1 shows a simplified schematic side view of an embodiment of a multipurpose measurement instrument according to the invention.

According to FIG. 1, a multipurpose measurement instrument 1 is provided for use in a knee-joint replacement operation. Different surgical techniques have been established for such knee-joint replacement operations. One technique is known in surgical practice as kinematic alignment TKA (total knee arthroplasty). The multipurpose measurement instrument 1 is provided especially for use in such a kinematically aligned TKA. In the text below, said surgical approach is also designated for short as kinematic alignment. Kinematic alignment comprises several intraoperative measurement and verification steps. For example, at the start of the surgical intervention, the anterior-posterior distance between the distal femur F and the proximal tibia T is determined under flexion (see FIG. 2). This distance is also referred to as the AP offset W. At the end of the surgical intervention, the AP offset is often measured and compared against the value measured at the start. Moreover, kinematic alignment comprises a resection of the distal femur F, the resection being followed by measurement of the thickness D of the sectioned bone, i.e. the femoral bone resection R (see FIG. 3). The multipurpose measurement instrument 1 serves on the one hand for the measurement of the AP offset and on the other hand for said thickness measurement.

The multipurpose measurement instrument 1 has a rod 2, a slide 3, a scale S formed between the rod 2 and the slide 3, and a continuation part 4.

The rod 2 extends along a longitudinal axis X between a first end 5 and a second end 6. At one end, the rod 2 has a first jaw 7. The first jaw 7 is arranged in the region of the second end 6. The first jaw 7 protrudes from the rod 2 along a transverse axis Y, which is oriented orthogonally with respect to the longitudinal axis X. More precisely, the first jaw 7 protrudes from the second end 6 of the rod 2 along the transverse axis Y. The first jaw 7 has a first inner surface 8. The first inner surface 8 extends rectilinearly and parallel to the transverse axis Y and is configured to bear on a front face V of the bone resection R (see FIG. 3).

The slide 3 is guided linearly movably on the rod 2 along the longitudinal axis X. The linear guiding of the slide 3 on the rod 2 is different in different embodiments.

In the embodiment shown, the rod 2 has a first guide path 9 and a second guide path 10. The first guide path 9 and the second guide path 10 each extend parallel to the longitudinal axis X between the first end 5 and the second end 6 and lie opposite each other along the transverse axis Y. The slide 3 has a first guide surface 11 and a second guide surface 12. The two guide surfaces 11, 12 extend parallel to the longitudinal axis X and are arranged opposite each other with respect to the transverse axis Y. The first guide surface 11 is movable by sliding along the first guide path 9. The second guide surface 12 is movable by sliding along the second guide path 10. At the same time, the slide 3 is held by form-fit engagement between the two guide paths 9, 10 with respect to the transverse axis Y. The detailed function and structural set-up of the linear guide for the slide is not essential for the present invention. Further explanations in this connection can therefore be omitted.

The slide 3 extends along the longitudinal axis X between its first end 13 and its second end 14 and has a second jaw 15 protruding from the second end 14 in a manner parallel to the transverse axis Y. The second jaw 15 has a second inner surface 16, which extends rectilinearly and parallel to the transverse axis Y and is oriented counter to the first inner surface 8. The second inner surface 16 is configured to bear on a rear face H of the bone resection R (see FIG. 3).

The first jaw 7 and the second jaw 15 each protrude from the rod 2 and from the slide 3, respectively, parallel to the transverse axis Y in a common direction. With respect to the drawing plane of FIG. 1, both jaws 7, 8 protrude downwards. The first inner surface 8 and the second inner surface 16 extend parallel to each other and are oriented counter to each other. With respect to the drawing plane of FIG. 1, the first inner surface 8 faces to the left, and the second inner surface 16 faces to the right.

Figure 3:
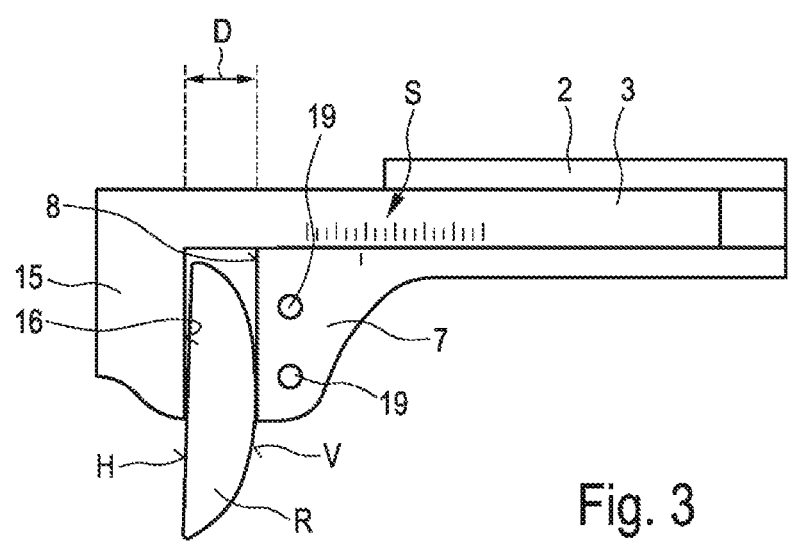
FIG. 3 shows a simplified schematic view of a second intraoperative situation, in which the multipurpose measurement instrument according to FIGS. 1 and 2 is used to measure the thickness of a femoral bone resection.

The scale S is formed between the rod 2 and the slide 3 and is configured to indicate the thickness D of the bone resection R (see FIG. 3). For this purpose, the scale S is assigned to the first inner surface 8 and to the second inner surface 16 and shows the distance A between them with respect to the longitudinal axis X. Various possibilities concerning the design of the scale S will be known in principle to a person skilled in the art.

In the embodiment shown, the scale S has a plurality of graduation lines S1 arranged in succession along the longitudinal axis X. Moreover, the scale S has a read-off marker S2 arranged on the rod 2. The distance A that is present and/or measured in each case can be read off on the read-off marker S2, to be more precise on the graduation line located immediately above the read-off marker S2.

The continuation part 4 is connected releasably to the first jaw 7 and has a third inner surface 17. The third inner surface 17 extends rectilinearly and parallel to the transverse axis Y and is configured to bear on the proximal tibia T (see FIG. 2). With respect to the transverse axis Y, the continuation part 4 protrudes further from the rod 2 than does the first jaw 7. Both the first jaw 7 and the continuation part 4 protrude on one and the same side of the rod 2. In the present case, and with respect to the drawing plane of FIG. 1, the first jaw 7 and the continuation part 4 each protrude and/or face downwards. Along the transverse axis Y, the third inner surface 17 is therefore spaced further from the longitudinal axis X than is the first inner surface 8.

The second jaw 15 has a second outer surface 18, which extends rectilinearly and parallel to the second inner surface 16 and is oriented counter to the latter. The second outer surface 18 is configured to bear on the distal femur F (see FIG. 2).

The first inner surface 8 and the third inner surface 17 are spaced apart from each other along the longitudinal axis X by a distance B. The second inner surface 16 and the second outer surface 18 are likewise spaced apart from each other by the distance B. As a result of this paired identical spacing between the first inner surface 8 and the third inner surface 17 on the one hand and the second inner surface 16 and the second outer surface 18 on the other hand, with respect to the longitudinal axis X, the scale S is additionally configured to indicate the longitudinal distance between the third inner surface 17 and the second outer surface 18. In other words, the first inner surface 8 and the second inner surface 16, on the one hand, and the third inner surface 17 and the second outer surface 18, on the other hand, are at all times spaced apart from each other by the (modifiable) distance A.

The scale S is therefore configured to indicate both the AP offset W and the thickness D.

Figure 2:
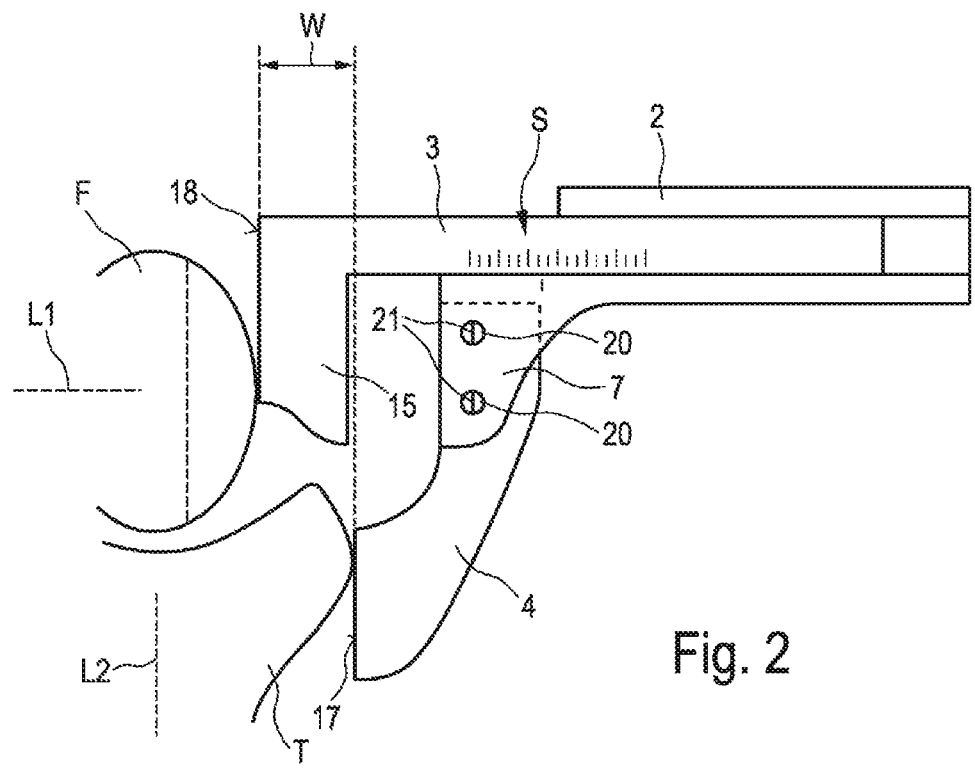
FIG. 2 shows a simplified schematic view of a first intraoperative situation, in which the multipurpose measurement instrument according to FIG. 1 is used to measure the AP offset between the distal femur and the proximal tibia.

As is shown in FIGS. 2 and 3, the measurement of the AP offset W, on the one hand, and the measurement of the thickness D of the bone resection R, on the other hand, take place here in different configurations of the multipurpose measurement instrument 1. Said configurations can also be referred to as a first configuration (FIG. 2) and a second configuration (FIG. 3).

In the first configuration, the continuation part 4 is connected releasably to the first jaw 7. To measure the AP offset W, the multipurpose measurement instrument 1 is placed manually, with the third inner surface 17 to the front, onto the proximal tibia T. The longitudinal axis X of the multipurpose measurement instrument 1 is preferably oriented parallel to a longitudinal axis L1 of the femur. The measurement of the AP offset W usually takes place under flexion, such that a longitudinal axis L2 of the tibia is oriented approximately orthogonal to the longitudinal axis L1 of the femur and thus also to the longitudinal axis X of the multipurpose measurement instrument 1. After the third inner surface 17 is placed on the proximal tibia T, the slide 3 is moved relative to the rod 2 in the direction of the distal femur F until the second outer surface 18 makes contact. The AP offset W can then be read off on the scale S in the manner described above.

In the further course of the kinematic alignment, the distal femur is usually resected. The resection is usually made orthogonally to the longitudinal axis L1 of the femur, as is indicated in FIG. 2 by means of the dashed line shown there. The resulting bone resection R is shown in FIG. 3. The thickness D of the bone resection R is measured in the second configuration of the multipurpose measurement instrument 1.

In the second configuration, the continuation part 4 is released and/or removed from the first jaw 7. For measuring the thickness, the bone resection R is put between the first jaw 7 and the second jaw 15, and the slide 3 is displaced longitudinally relative to the rod 2 in the direction of the first end 5. That is until the first inner surface 18 comes to bear on the front face V and the second inner surface 16 comes to bear on the rear face H of the bone resection R. The (maximum) longitudinal distance between the front face V and the rear face H corresponds to the thickness D, which can be read off the scale S in the manner described above.

For renewed measurement of the AP offset on the implanted artificial joint component, the continuation part 4 can again be connected to the first jaw 7, proceeding from the second configuration.

As can further be seen from FIGS. 2 and 3, the first inner surface 8 is unsuitable for measuring the AP offset. Rather, a certain transverse distance of the instrument's contact face from the longitudinal axis X is required in order to permit simultaneous contact on the distal femur F, on the one hand, and the proximal tibia T, on the other hand. For this purpose, the continuation part 4 protrudes further from the longitudinal axis X than does the first jaw 7. Conversely, a thickness measurement between the third inner surface 17 and the second inner surface 16 is not possible (FIG. 2). This is because said inner surfaces do not lie directly opposite each other. Rather, with respect to the transverse axis Y, the third inner surface 17 is offset downwards relative to the second inner surface 16, and vice versa. For this purpose by contrast, the first inner surface 8 and the second inner surface 16 lie directly opposite each other. This permits correct measurement of thickness (see FIG. 3). For this purpose, the continuation part 4 is easily removable.

To allow it to be attached to and removed from the first jaw 7 as easily as possible, the continuation part 4 is connected to the first jaw 7 by means of a tool-free first joining connection C1. Tool-free means that the first joining connection C1 is releasable and connectable without the use of a tool.

The first joining connection C1 is differently configured in different embodiments and can be, for example, a latching, plug-in or clamping connection.

In the embodiment shown, the first joining connection C1 is a plug-in connection. The plug-in connection is formed between suitable portions and/or structural parts of the first jaw 7, on the one hand, and of the continuation part 4, on the other hand.

In the embodiment shown, the first joining connection C1 has two first bores 19 and two first pin elements 20. The first bores 19 and the first pin elements 20 are plugged together orthogonally with respect to the longitudinal axis X and orthogonally with respect to the transverse axis Y. In the present case, the first bores 19 are introduced into the first jaw 7 (see FIG. 3). The first pin elements 20 are connected permanently to the connection part 4 and, in the embodiment shown, are formed in one piece thereon. The first bores 19 are each designed as a through-bore and extend all the way between mutually opposite outer faces of the first jaw 7. The first pin elements 20 each protrude from the continuation part 4 laterally and orthogonally with respect to the longitudinal axis and to the transverse axis. The first pins 20, more precisely the outer circumference and/or diameter thereof, are adapted in size to the first bores 19, and vice versa. In particular, the diameter of the first pin elements 20 is slightly greater than the internal diameter of the first bores 19. This ensures a firm but still releasable fit of the continuation part 4.

It will be appreciated that different embodiments can have different numbers of bores and pin elements. Therefore, in an embodiment not shown in the figures, only a single bore and a single pin element are present.

In the embodiment shown, the first pin elements 20 each have a slit 21 introduced into one end face. The slit 21 supports a resilient spring movement of the first pin elements 20 in a radial direction. This resilient spring movement ensures sufficient yield when the first pin elements 20 are plugged into the first bores 19.

Figure 4:
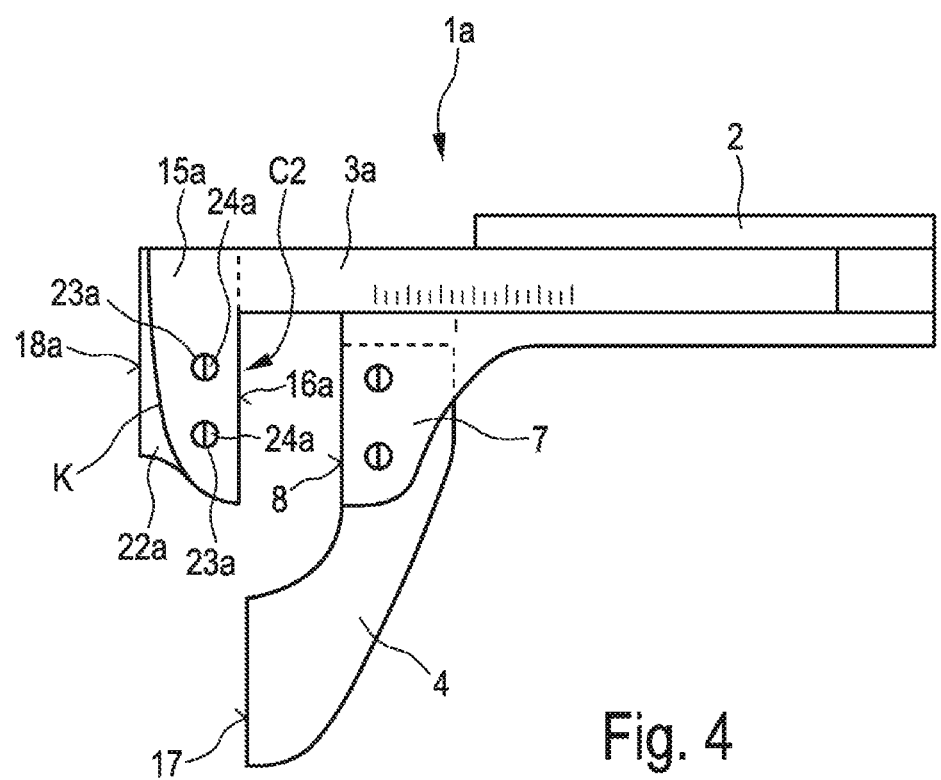
FIG. 4 shows, in a view corresponding to FIG. 1, a further embodiment of a multipurpose measurement instrument according to the invention.

FIG. 4 shows a further embodiment of a multipurpose measurement instrument 1a according to the invention. The multipurpose measurement instrument 1a according to FIG. 4 largely corresponds to the multipurpose measurement instrument 1 according to FIGS. 1 to 3. Only essential differences of the multipurpose measurement instrument 1a according to FIG. 4 in relation to the multipurpose measurement instrument 1 are discussed below. Identical structural parts and/or portions are provided with identical reference signs and are not explained separately. As regards their design and/or function, different structural parts and/or sections are identified with identical reference signs with addition of a lower case letter.

The multipurpose measurement instrument 1a differs from the multipurpose measurement instrument 1 in having a differently designed slide 3a. The slide 3a has a second jaw 15a. The second jaw 15a has an outer contour K that is not configured to bear on the distal femur F. The outer contour K is inclined and/or curved. Said inclination and/or curvature prevents it from bearing correctly on the distal femur (see FIG. 2). In order nonetheless to permit a measurement of the AP offset W, the multipurpose measurement instrument 1a has an extension part 22a which is connected releasably to the second jaw 15a and on which the second outer surface 18a is formed. As regards the remaining function and design of the second outer surface 18a, reference is made to what has been said concerning the embodiment according to FIGS. 1 to 3.

In contrast to the outer contour K, the second outer surface 18 is rectilinear and parallel to the transverse axis Y. This allows it to bear correctly on the distal femur F. The outer contour K is covered at least in part by the second outer surface 18a. In other words, the extension part 22a protrudes over the second jaw 15a with respect to the longitudinal axis X. The extension part 22a in this sense forms a front end face of the multipurpose measurement instrument 1a.

The extension part 22a is connected releasably to the second jaw 15a by means of a second joining connection C2. The second joining connection C2 is designed differently in different embodiments. A latching, clamping or plug-in connection is again conceivable.

In the embodiment shown, the second joining connection C2 is designed analogously to the first joining connection C1 and accordingly has two second bores 23a and two second pin elements 24a. To avoid repetition, reference is otherwise made to what has been said concerning the first joining connection.

In the embodiments shown, the rod 2 and the respective slide 3, 3a are each made of metal. The continuation part 4 and the extension part 22a are each made of plastic. By being made of metal, the arrangements composed of rod 2 and of slide 3, 3a are each configured for repeated use. By contrast, the continuation part 4 and the extension part 22a are disposable parts, i.e., provided to be used just once.

The invention claimed is:

1. A measurement instrument for use in a knee-joint replacement operation, the measurement instrument comprising:
    a rod extending along a longitudinal axis, the rod comprising a first jaw at one end, the first jaw protruding along a transverse axis and comprising a first inner surface that extends parallel to the transverse axis, the first inner surface configured to bear on a front face of a bone resection;
    a slide that is guided linearly movably on the rod along the longitudinal axis, the slide comprising a second jaw at one end, the second jaw protruding along the transverse axis and comprising a second inner surface that extends parallel to the transverse axis, the second inner surface oriented counter to the first inner surface and configured to bear on a rear face of the bone resection;
    a scale formed between the rod and the slide, the scale configured at least to indicate a thickness of the bone resection along the longitudinal axis; and
    a continuation part connected releasably to the first jaw, the continuation part comprising a third inner surface configured to bear on a proximal tibia, the third inner surface extending parallel to the transverse axis and protruding further from the rod than the first inner surface,
    the second jaw comprising a second outer surface extending parallel to the transverse axis, the second outer surface oriented counter to the second inner surface and configured to bear on a distal femur,
    the third inner surface and the first inner surface being spaced apart from each other along the longitudinal axis by a first distance,
    the second inner surface and the second outer surface being spaced apart from each other along the longitudinal axis by a second distance identical to the first distance,
    the scale configured to indicate a longitudinal distance between the distal femur and the proximal tibia.

2. The measurement instrument according to claim 1, wherein the continuation part is connected to the first jaw by a first joining connection that is releasable without tools and connectable without tools.

3. The measurement instrument according to claim 2, wherein the first joining connection has at least a first bore and a first pin element that are releasably plugged together orthogonally with respect to the longitudinal axis and the transverse axis, wherein the first bore is introduced into the first jaw, and the first pin element is rigidly connected to the continuation part, or vice versa.

4. The measurement instrument according to claim 1, wherein the second outer surface is formed on an extension part connected releasably to the second jaw, wherein the second jaw has an inclined and/or curved outer contour which is not configured to bear on the distal femur and which is covered at least in part by the second outer surface.

5. The measurement instrument according to claim 4, wherein the extension part is connected to the second jaw by a second joining connection that is releasable without tools and connectable without tools.

6. The measurement instrument according to claim 5, wherein the second joining connection has at least a second bore and a second pin element that are releasably plugged together orthogonally with respect to the longitudinal axis and the transverse axis, wherein the second bore is introduced into the second jaw, and the second pin element is rigidly connected to the extension part, or vice versa.

7. The measurement instrument according to claim 1, wherein the rod and the slide are each made of metal and are configured for repeated use, and the continuation part and/or the extension part are/is made of plastic and configured to be used just once.

\* \* \* \* \*